(12) United States Patent
Bankers et al.

(10) Patent No.: US 7,600,697 B2
(45) Date of Patent: Oct. 13, 2009

(54) VAPOR-EMITTING DEVICE WITH END OF USE INDICATOR

(75) Inventors: Jeffrey Bankers, Phoenix, AZ (US); Debbie Butterworth, Scottsdale, AZ (US); Geoffrey Faires, Cave Creek, AZ (US)

(73) Assignee: The Dial Corporation, Scottsdale, AZ (US)

( * ) Notice: Subject to any disclaimer, the term of this patent is extended or adjusted under 35 U.S.C. 154(b) by 167 days.

(21) Appl. No.: 11/799,913

(22) Filed: May 3, 2007

(65) Prior Publication Data

US 2008/0272201 A1 Nov. 6, 2008

(51) Int. Cl.
*A24F 25/00* (2006.01)

(52) U.S. Cl. .............................. 239/35; 239/34; 239/60; 239/71

(58) Field of Classification Search .................... 239/34, 239/35, 57, 58, 60, 71, 73, 74; 424/76.3, 424/76.4; 423/123; 116/200
See application file for complete search history.

(56) References Cited

U.S. PATENT DOCUMENTS

| 3,104,816 | A | * | 9/1963 | Jaffe ............................ 239/35 |
| 5,163,616 | A | * | 11/1992 | Bernarducci et al. .......... 239/35 |
| 5,180,107 | A | | 1/1993 | Lindauer |
| 5,647,052 | A | | 7/1997 | Patel et al. |
| 7,033,990 | B2 | | 4/2006 | Dundale et al. |
| 7,159,792 | B2 | | 1/2007 | Wheatley et al. |
| 2003/0175172 | A1 | * | 9/2003 | Altmann ...................... 239/60 |
| 2006/0100303 | A1 | | 5/2006 | Bedford et al. |
| 2006/0102738 | A1 | | 5/2006 | Gusenoff et al. |

* cited by examiner

*Primary Examiner*—Steven J Ganey
(74) *Attorney, Agent, or Firm*—Paul A. Pappalardo

(57) ABSTRACT

A vapor-emitting device according to various embodiments of the invention includes an end of use indicator to visually warn a user that it is nearing the time and/or has reached the time to replace the vapor-emitting device or refill the device. The vapor-emitting device includes a cover that is displaceable relative to a base. A gel material is contained within the base having disposed therein an end of use indicator. The end of use indicator is configured to visually indicate when the gel material evaporates below a pre-determined level.

18 Claims, 2 Drawing Sheets

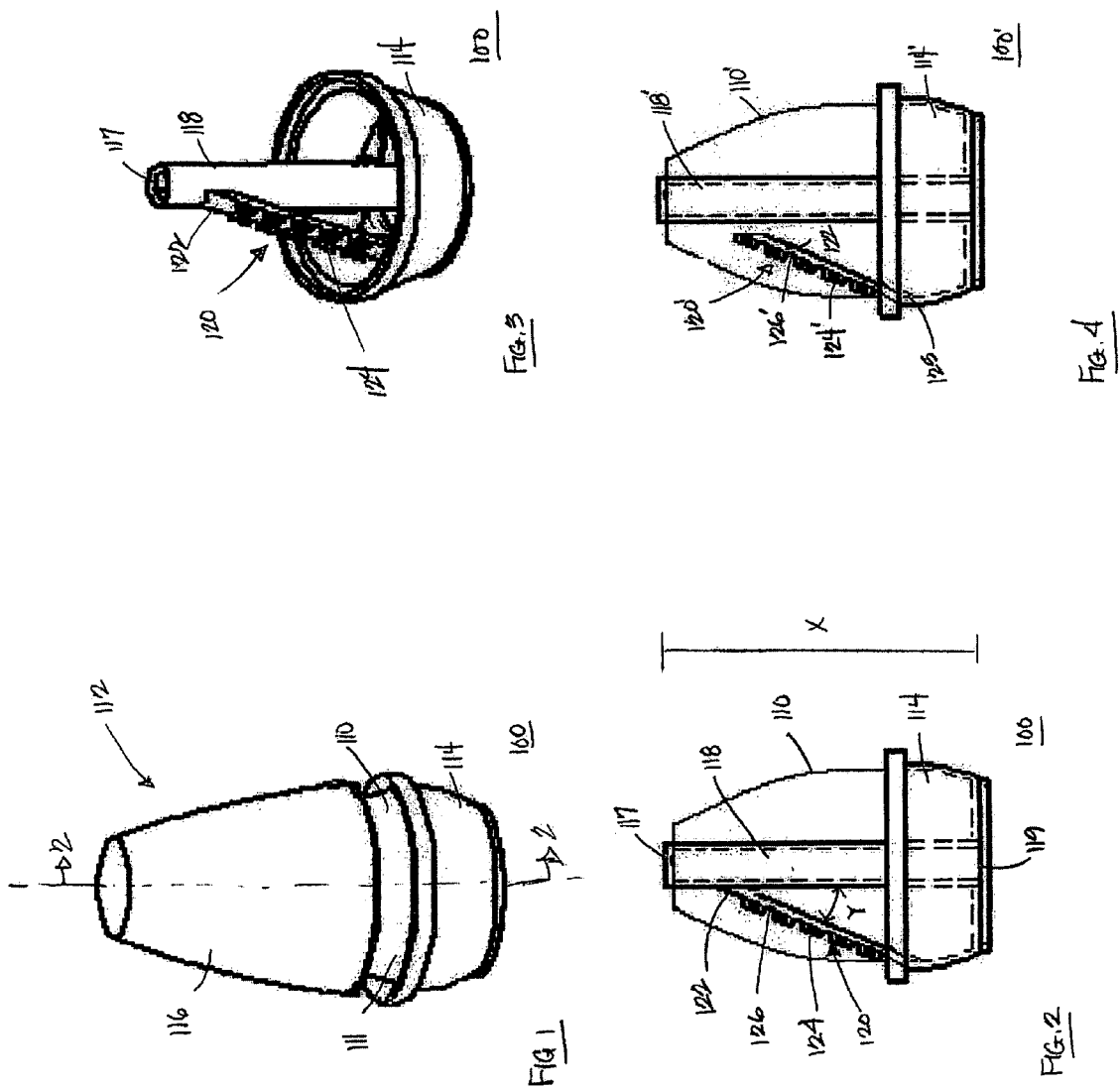

VAPOR-EMITTING DEVICE WITH END OF USE INDICATOR

FIELD OF THE INVENTION

The present invention relates to vapor-emitting devices, and more particularly to, a vapor-emitting device which includes a gel-type solid or semi-solid mass of material which is designed to release a volatile active ingredient over time, wherein the device includes an end of use indicator.

BACKGROUND OF THE INVENTION

Vapor-emitting devices are generally used to emit an environment-altering fragrance, an insect repellant, and/or the like into the atmosphere. In general, a vapor-emitting device operates by releasing a fragrance or other volatile active ingredient that is encompassed within a solid or semi-solid gel material. This process occurs through vaporization/evaporation over an extended time period. The vapor-emitting device may provide, amongst other things, the release of a pleasing fragrance or a material to counter offensive odors into the atmosphere. During use the contents of the vapor-emitting device, and more particularly the solid or semi-solid gel material that encompasses the fragrance or other volatile active ingredient, gradually decreases until it is to replace or refill the device. In order to make the determination of when it is time to replace the vapor-emitting device, or refill it if possible, users are required to take the initiative to visually inspect the contents of the vapor-emitting device. There are, however, at least a few problems associated with such a requirement, one of the most critical being that upon inspection, the user must have the capability of determining that indeed the vapor-emitting device contains a low amount of solid or semi-solid gel material and thus a low amount of volatizable ingredient and is no longer capable of emitting a vapor.

As described above, current devices do not include a means for visually alerting the user that the vapor-emitting device is low on gel material and thus volatizable ingredient and is no longer capable of producing vapor. Accordingly, there is a need for a vapor-emitting device that includes a visual end of use indicator that warns the users that the device is low on volatizable ingredient and/or no longer producing vapor such that users will be put on notice that it is nearing the time, or is time, to replace or refill the vapor-emitting device.

It should thus be appreciated from the above that it would be desirable to provide a vapor-emitting device that includes an end of use indicator that upon visual inspection the user is able to determine the need for replacement or refill of the vapor-emitting device. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

There has now been developed a vapor-emitting device according to various exemplary embodiments of the present invention. In one embodiment, the vapor-emitting device includes a housing comprising a cover and a base. The cover is displaceable along a vertical axis relative to the base. A gel material is contained therein the housing and configured to evaporate when exposed to an external environment. An end of use indicator is positioned within the gel material and coupled to the base. The end of use indicator is configured to visually indicate when the gel material evaporates below a pre-determined level.

In yet another embodiment, there is provided a vapor-emitting device comprised of a housing including a cover and a base, a vertical support member, a gel material and an end of use indicator. The cover is displaceable along a vertical axis, relative to the base. The vertical support member is coupled to the base. The gel material includes a volatizable ingredient contained therein and is formed about the vertical support. The gel material is configured to evaporate when the cover is displaced relative to the base, thereby exposing the gel material to an external environment. The end of use indicator is coupled to at least a portion of the housing and configured to alert a user that the gel material has evaporated to a pre-determined level. The end of use indicator is comprised of an indicia strip positioned within the gel material and at an angle relative to the vertical axis and includes at least one indicia formed on and protruding therefrom a surface of the indicia strip. The at least one indicia is visible when the gel material has evaporated to the pre-determined level.

In a further embodiment, still by way of example only, there is provided a vapor-emitting device comprised of a substantially cone-shaped housing including a cover and a base, a gel material including a volatizable ingredient contained therein the housing, and an end of use indicator coupled to the base and configured to alert a user that the gel material has evaporated to a pre-determined level. The cover is displaceable relative to the base along a vertical axis. The gel material is configured to evaporate when the cover is displaced relative to the base, thereby exposing the gel material to an external environment. The end of use indicator is comprised of an indicia strip positioned within the gel material at an angle relative to the vertical axis of the vapor-emitting device and coupled to the a portion of the housing. The indicia strip includes at least one indicia formed on and protruding therefrom a surface of the indicia strip. During use, the gel material evaporates and binds about the indicia strip, exposing the at least one indicia and visually indicating the gel material has reached the pre-determined level.

Other independent features and advantages of the improved vapor-emitting device will become apparent from the following detailed description, taken in conjunction with the accompanying drawings which illustrate, by way of example, the principles of the invention.

BRIEF DESCRIPTION OF THE DRAWINGS

The present invention will hereinafter be described in conjunction with the following drawing figure, wherein like numerals denote like elements. Additional embodiments of the invention will become evident upon reviewing the non-limiting embodiments described in the specification in conjunction with the accompanying figures, wherein:

FIG. 1 is a diagram of an exemplary embodiment of a vapor-emitting device including an end of use indicator according to the present invention;

FIG. 2 is a partial cross-sectional view taken along line 2-2 of FIG. 1 showing a portion of the vapor-emitting device including an end of use indicator according to the present invention;

FIG. 3 is isometric view of a portion of the vapor-emitting device of FIG. 1, including an end of use indicator according to the present invention;

FIG. 4 is a partial cross-sectional view of yet another embodiment of a portion of a vapor-emitting device including an end of use indicator according to the present invention;

DETAILED DESCRIPTION OF THE INVENTION

Figure 6:
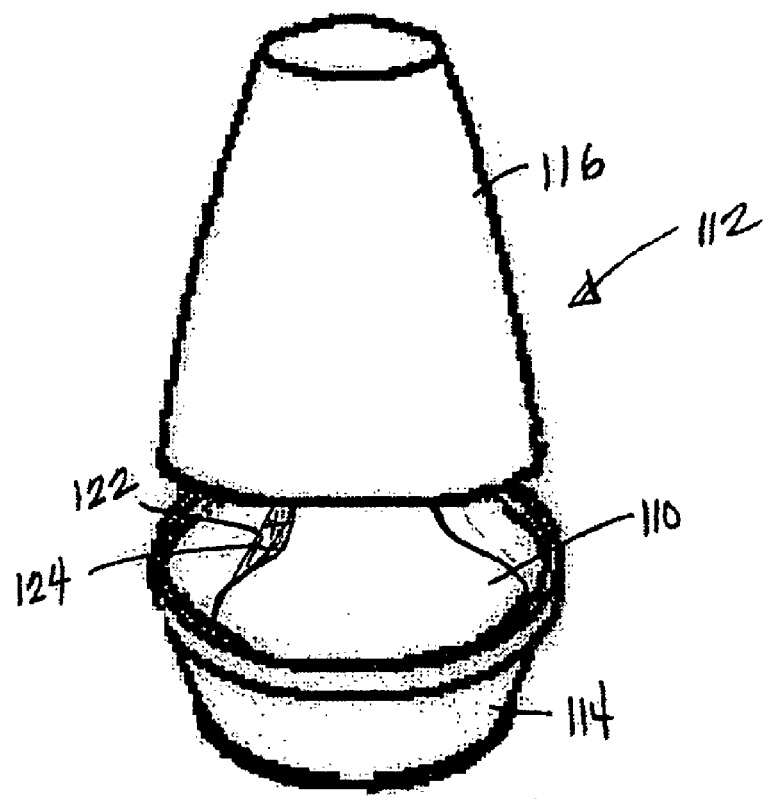
FIG. 6 is an isometric view of a portion of the vapor-emitting device of FIG. 1 including an end of use indicator having been exposed to an external environment for a period of time.

The following detailed description of the invention is merely exemplary in nature and is not intended to limit the invention or the application and uses of the invention. Furthermore, there is no intention to be bound by any theory presented in the preceding background of the invention or the following detailed description of the invention. In this regard, before proceeding with the detailed description, it is to be appreciated that the described exemplary embodiments are not limited to use in conjunction with a specific vapor-emitting device. Thus, although the description is explicitly directed toward an embodiment that is implemented in a specifically shaped vapor-emitting device, it should be appreciated that it can be implemented in many types of vapor-emitting devices, including those known now or hereafter in the art.

The detailed description of exemplary embodiments of the invention herein makes reference to the accompanying figures, which show the exemplary embodiments by way of illustration and its best mode. While the exemplary embodiments are described in sufficient detail to enable one skilled in the art to practice the invention, it should be understood that other embodiments may be realized, and that logical and/or mechanical changes may be made without departing from the spirit and scope of the invention. Thus, the detailed description herein is presented for purposes of illustration only and not by way of limitation.

The invention includes a vapor-emitting device (e.g., air freshener, emanator, evaporator, and the like). In an exemplary embodiment, the vapor-emitting device is configured to alert a user that it is time and/or nearing the time to refill the device, or replace the device. To alert the user, the vapor-emitting device includes an end of use indicator that initially becomes visible when a pre-determined level of a gel material including a volatizable ingredient has been reached in the device.

Turning now to the figures, FIG. 1 is a diagram of an exemplary embodiment of a vapor-emitting device 100 including an end of use indicator. Vapor-emitting device 100 may be any device and/or components known in the art capable of evaporating a volatizable ingredient (e.g., a fragrance, insecticide, insect repellant, and the like). In this exemplary embodiment, vapor-emitting device 100 includes a gel material 110, typically in the form of a solid or semi-solid material, having an active or volatizable ingredient, 111 contained therein. Vapor-emitting device 100 in this exemplary embodiment is a passive vapor-emitting device such that gel material 110, and thus the volatizable ingredient 111, is caused to be evaporated and/or vaporized.

Vapor-emitting device 100 includes a housing 112, typically comprising a base 114 and a cover 116. Cover 116 is manually displaceable with respect to base 114, as indicated by a directional arrow in FIG. 1. More specifically, cover 116 is displaceable along a vertical axis of the vapor-emitting device 100 to control the effective rate of volatilization or evaporation of the gel material 110, and more particularly the volatizable ingredient 111. In the embodiment illustrated in FIG. 1, cover 116 is illustrated in a partially open position. Gel material 110 may include any volatizable ingredient 111 known in the art capable of, for example, altering the scent in an environment (e.g., a fragrance) and/or discouraging insects and the like from being present in the environment (e.g., an insecticide, an insect repellant, and the like). In this exemplary embodiment, gel material 110 is a carrageenan gel that when given a surface to attach to, will spread over the surface as it evaporates and/or vaporizes. Gel material 110, including volatizable ingredient 111, to which the present invention applies are well known in the art, as are the methods of manufacture and positioning in a housing such as housing 112 shown in FIG. 1.

In this exemplary embodiment, vapor-emitting device 100, and more particularly housing 112, is generally formed as a cone-shaped device. It should be understood that although housing 112 is disclosed as being generally cone-shaped, alternative shapes for housing 112 are anticipated by this disclosure. In a preferred embodiment, base 114 and cover 116 are formed of a molded plastic material, although other suitable materials are anticipated by this disclosure.

Referring now to FIGS. 2 and 3, illustrated in a cross-section view taken along line 2-2 of FIG. 1, and in an isometric view, respectively, is the exemplary embodiment of vapor-emitting device 100. For purposes of illustration, in FIG. 2 a portion of housing 112, and more particularly cover 116 is not shown, and in FIG. 3 cover 116 and gel material 110 are not shown. In accordance with this exemplary embodiment, housing 112 includes therein a centrally located support member 118, or a plurality of support members, around which the gel material 110, including volatizable ingredient 111, is molded or formed. Support member 118 provides vertical support and strength to gel material 110 housed within housing 112 and enables displacement of cover 116 (not shown). Support member 118 may be formed as an integral member with housing 112, and more particularly base 114, or in the alternative separately formed and positioned in place during assembly of housing 112. Support member 118 is formed having a first end 117 and a second end 119, separated by a length "x". In this particular embodiment, second end 119 is coupled to base 114 as illustrated.

Vapor-emitting device 100 further includes an end of use indicator 120 to alert a user that housing 112 includes a low level of gel material 110, and thus a low level of volatizable ingredient 111 and/or is empty. In the exemplary embodiment, end of use indicator 120 is formed as an indicia strip 122, generally in the shape of a fin that is statically coupled at opposed end portions to support member 118 and base 114. Indicia strip 120 includes at least one visible indicia 124, generally in the form of a raised element that protrudes from a surface 126 of indicia strip 122. In this particular embodiment, at least one visible indicia 124 is in the form of a plurality of X's that form the visual end of use indicator 120 as described below.

Indicia strip 122 is positioned relative to support member 118 at an angle dependent upon the design of the overall vapor-emitting device 100 and the evaporative properties of gel material 110. More specifically, as best illustrated in FIG. 2, when gel material 110 is initially formed, indicia strip 120 is positioned within gel material 110 and at an angle Y, relative to support member 118, to allow for complete coverage of the at least one indicia 124 formed thereon by gel material 110.

Illustrated in FIG. 4 is a cross-section of a vapor-emitting device according to another embodiment of the present invention. It should be noted that all components of FIG. 4 that are similar to the components illustrated in FIGS. 1-3, are designated with similar numbers, having a prime added to indicate the different embodiment. In this particular embodiment, a vapor-emitting device 100' including an end of use indicator 120' is shown. End of use indicator 120' is comprised of an indicia strip 122' and at least one visible indicia 124' protruding from a surface 126' of the indicia strip 122'. Indicia strip 122' is statically coupled to a base 114' at an end portion 125 and is positioned within a gel material 110'. In contrast to the previously described embodiment, indicia strip 122' is not statically coupled to a support member 118'. It is additionally anticipated by this disclosure that in yet another embodiment of the vapor-emitting device of the present invention that the indicia strip 122' is statically coupled to the support member 118' and not statically coupled to the base 114'.

Figure 5:
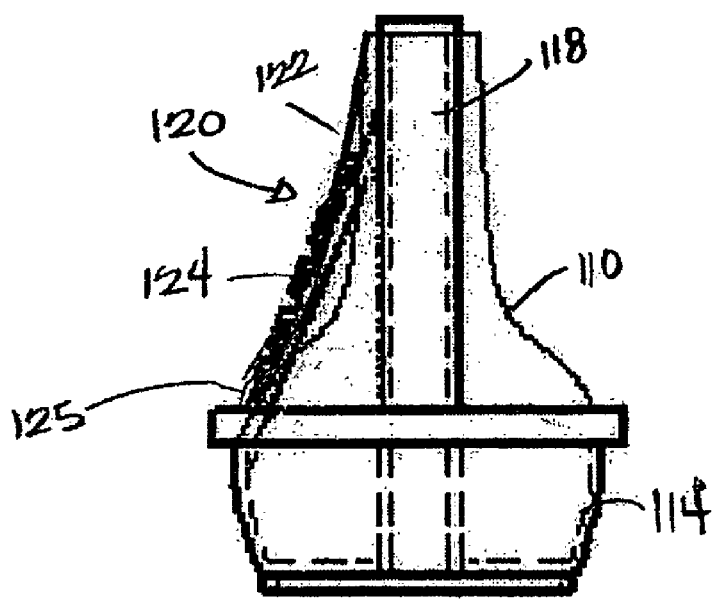
FIG. 5 is a partial cross-sectional view of a portion of a vapor-emitting device including an end of use indicator having been exposed to an external environment for a period of time.

Referring now to FIGS. 5 and 6, illustrated in cross-section and in isometric view, respectively, similar to FIGS. 2 and 3, is the exemplary embodiment of vapor-emitting device 100 after exposure to an external environment for a period of time. FIGS. 5 and 6 illustrate gel material 110 in a partially evaporated and/or vaporized state. More particularly, as gel material 110 evaporates and/or vaporizes, indicia strip 122 becomes exposed proximate the end portion 125 that is positioned the furthest away from the support member 118. It should be noted that gel material 110 will undergo a reliable geometric/conformational change during use dependent upon the design of the vapor-emitting device 100. Accordingly, the indicia strip 120 is positionable in reliance upon this geometric/conformational change. As illustrated, during evaporation and/or vaporization of gel material 110, the at least one indicia 124 becomes exposed, or visually revealed.

The reveal of indicia 124 on indicia strip 122 may be designed to provide an indication of the intensity of the remaining fragrance, etc., and/or a time period remaining prior to the depletion of gel material 110. For instance, during use of vapor-emitting device 100, gel material 110 gradually evaporates and binds across indicia strip 122. In the illustrated exemplary embodiment, indicia strip 122 includes a plurality of visual indicia 124 in the form of raised X's along the length of indicia strip 122. When e gel material 110 begins to bind across indicia strip 122, a first X indicia 124 will be exposed. This may provide a visual indication to the user of a remaining time period in which gel material 110 will be present, or a visual indicator as to the remaining intensity of volatizable ingredient 111 contained therein gel material 110. As subsequent indicia 124, or X's, are exposed, the user may become visually aware of the time period remaining, or the intensity of volatizable ingredient 111. It should be understood that while indicia 124 in this exemplary embodiment are in the form of X's, any type of indicia 124 that is raised from the surface of indicia strip 122 thus providing a binding surface for the gel material 110 may be used. More particularly, it is anticipated that letters and/or numbers may be used to visibly indicate information to the user. For example, in another exemplary embodiment, end of use indicator 120, and more specifically indicia strip 122 may have formed on its visible surface a series of raised letters and/or numbers indicating for example a one week, two week, etc. or remaining life of gel material 110.

Various embodiments of vapor-emitting device 100 function such that when sufficient gel material 110 is remaining within housing 112, the indicia 124 on indicia strip 122 is not visible. However, when gel material 110 is partially used, or sufficient gel material 110 is not present within housing 112 such that the efficiency of the vapor-emitting device 100 is affected, indicia strip 122 is configured to make visible the indicia 124 formed thereon to alert the user that vapor-emitting device 100 needs to be replaced or refilled.

Accordingly, disclosed is an improved vapor-emitting device including a visual end of use indicator. While exemplary embodiments have been presented in the foregoing detailed description of the invention, it should be appreciated that a vast number of variations exist. In addition, benefits, other advantages, and solutions to the problem have been described herein with regard to exemplary embodiments. However, the benefits, advantages, solutions to problems, and any element(s) that may cause any benefit, advantage, or solution to occur or become more pronounced are not to be construed as critical, required, or essential features or elements of any or all the claims or the invention. It should also be appreciated that the exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims.

What is claimed is:

1. A vapor-emitting device comprising:
a housing comprising a cover and a base, wherein the cover is displaceable along a vertical axis relative to the base;
a gel material contained therein the housing, the gel material configured to evaporate when exposed to an external environment; and
an end of use indicator positioned within the gel material and coupled to the base, said end of use indicator including an indicia strip having at least one indicia formed on and protruding therefrom a surface of the indicia strip, wherein said end of use indicator is configured to visually indicate when the gel evaporates to a pre-determined level.

2. The vapor-emitting device of claim 1, wherein the gel material includes a volatizable ingredient dispersed therein.

3. The vapor-emitting device of claim 2, wherein the volatizable ingredient is one of a fragrance, an insecticide, or an insect repellant.

4. The vapor-emitting device of claim 1, wherein the at least one indicia includes a plurality of visible indicia indicating the remaining period of use of the vapor-emitting device.

5. The vapor-emitting device of claim 1, further including a vertical support member coupled to the base, the gel material formed about the vertical support member.

6. The vapor-emitting device of claim 1, wherein the indicia strip is positioned within the material at an angle relative to the vertical axis of the vapor-emitting device and coupled to the base.

7. The vapor-emitting device of claim 1, wherein the indicia strip is additionally coupled to the vertical support member.

8. The vapor-emitting device of claim 1, wherein the indicia strip is positioned within the gel material at an angle relative to the vertical axis of the vapor-emitting device and coupled to the vertical support member.

9. A vapor-emitting device comprising:
a housing comprising a cover and a base, wherein the cover is displaceable along a vertical axis, relative to the ease;
a vertical support member coupled to the base;
a gel material including a volatizable ingredient contained therein, the gel material formed about the vertical support and configured to evaporate when the cover is displaced relative to the base exposing the gel material to an external environment; and
an end of use indicator coupled to at least a portion of the housing and configured to alert a user that the gel material has evaporated to a pre-determined level;
the end of use indicator comprising:
an indicia strip positioned within the gel material and at an angle relative to the vertical axis; and
at least one indicia formed on and protruding therefrom a surface of the indicia strip and visible when the gel material has evaporated to the pre-determined level.

10. The vapor-emitting device of claim 9, wherein the volatizable ingredient is one of a fragrance, an insecticide, or an insect repellant.

11. The vapor-emitting device of claim 9, wherein the indicia strip is statically coupled at a first end to the vertical support member and at a second end to the base.

12. The vapor-emitting device of claim 9, wherein the indicia strip is statically coupled at a second end to the base.

13. The vapor-emitting device of claim 9, wherein the housing is substantially cone-shaped.

14. The vapor-emitting device of claim 9, wherein the at least one indicia includes a plurality of indicia configured when visible to indicate the intensity of the volatizable ingredient.

15. The vapor-emitting device of claim 9, wherein the at least one indicia includes a plurality of indicia configured when visible to indicate the remaining period of use of the vapor-emitting device.

16. A vapor-emitting device comprising:
a substantially cone-shaped housing comprising a cover and a base, wherein the cover is displaceable relative to the base along a vertical axis;
a gel material including a volatizable ingredient contained therein the housing, the gel material configured to evaporate when the cover is displaced relative to the base, thereby exposing the gel material to an external environment; and
an end of use indicator coupled to the base and configured to alert a user that the gel material has evaporated to a pre-determined level, the end of use indicator comprising:
an indicia strip positioned within the gel material at an angle relative to the vertical axis of the vapor-emitting device and coupled to the portion of the housing; and
at least one indicia formed on and protruding therefrom a surface of the indicia strip,
wherein the gel material evaporates and binds about the indicia strip, exposing the at least one indicia and visually indicating the gel material has reached the pre-determined level.

17. The vapor-emitting device of claim 16, further including a vertical support member coupled to the base, the gel material formed about the vertical support member.

18. The vapor-emitting device of claim 17, wherein the indicia strip is further coupled to the vertical support member.

* * * * *